United States Patent [19]

Besecke et al.

[11] Patent Number: 4,647,696
[45] Date of Patent: Mar. 3, 1987

[54] METHOD FOR MAKING ISOBUTYRIC ACID

[75] Inventors: Siegmund Besecke, Darmstadt; Guenter Schroeder, Ober-Ramstadt; Hermann-Josef Siegert, Darmstadt; Wolfgang Gaenzler, Darmstadt-Arheilgen, all of Fed. Rep. of Germany

[73] Assignee: Röhm GmbH, Darmstadt, Fed. Rep. of Germany

[21] Appl. No.: 474,799

[22] Filed: Mar. 14, 1983

Related U.S. Application Data

[60] Continuation of Ser. No. 290,601, Aug. 6, 1981, abandoned, which is a division of Ser. No. 215,523, Dec. 11, 1980, abandoned.

[30] Foreign Application Priority Data

Dec. 20, 1979 [DE] Fed. Rep. of Germany ....... 2951289
Sep. 6, 1980 [DE] Fed. Rep. of Germany ....... 3033655

[51] Int. Cl.[4] .................... C07B 53/00; C07C 53/124
[52] U.S. Cl. .................................................. 562/606
[58] Field of Search ...................... 562/606, 517, 607

[56] References Cited

U.S. PATENT DOCUMENTS

| | | | |
|---|---|---|---|
| 2,975,199 | 3/1961 | Friedman et al. | 260/410.9 R |
| 3,052,698 | 9/1962 | Friedman et al. | 260/410.9 R |
| 3,839,428 | 10/1974 | Isogai | 562/517 |
| 3,910,963 | 10/1975 | Souma et al. | 260/343 |

FOREIGN PATENT DOCUMENTS

| | | | |
|---|---|---|---|
| 2026031 | 2/1971 | Fed. Rep. of Germany | 562/517 |
| 2240778 | 3/1973 | Fed. Rep. of Germany | 562/607 |
| 2750719 | 5/1979 | Fed. Rep. of Germany | 562/517 |

OTHER PUBLICATIONS

Koch et al, Ann. Chem., 618, 251-261, 1958.

Primary Examiner—Werren B. Lone
Attorney, Agent, or Firm—Curtis, Morris & Safford

[57] ABSTRACT

What is disclosed is a continuous one-step method for the preparation of isobutyric acid or a lower alkyl ester thereof by the Koch synthesis, which method comprises reacting propylene, carbon monoxide, and water or a lower alcohol, in the gaseous and liquid phases, in the presence of hydrogen fluoride as a Koch catalyst, at a temperature between 80° C. and 160° C., at a dwell time of the liquid phase of less than 20 minutes, and with a high degree of backmixing, while maintaining the content of propylene in the reaction mixture at less than one percent by weight of the liquid phase, wherein all or part of the propylene, carbon monoxide, and water or lower alcohol can be replaced by binary addition compounds formed pairwise between these materials. In the alternative, isopropylformiate can be continuously rearranged in the presence of hydrogen fluoride to produce isobutyric acid.

2 Claims, No Drawings

METHOD FOR MAKING ISOBUTYRIC ACID

This application is a continuation of Ser. No. 290,601 filed Aug. 6, 1981 and now abandoned, which in turn is a divisional of Ser. No. 215,523 filed Dec. 11, 1980 and now abandoned.

The present invention relates to an improved method for making isobutyric acid or its lower alkyl esters. These compounds can be converted by dehydrogenation into methacrylic acid or its lower alkyl esters, which latter materials are in turn starting materials for valuable synthetic resins.

The preparation of isobutyric acid by the Koch synthesis, starting from propylene, is known in the prior art. When water is used, isobutyric acid is obtained; when lower alkanols are used, particularly methanol, the corresponding lower alkyl esters are formed. One can also start with isopropyl alcohol and in this way obtains isobutyric acid without the use of water. As a Koch catalyst for these reactions, hydrogen fluoride, inter alia, is used.

The preparation of isobutyric acid or its esters by the Koch synthesis has until now not been realized on a technical scale. Although the reaction has been studied thoroughly and numerous method variants and experimental conditions have been tested, the high selectivity and yield coupled with a tolerable dwell time or space-time yield necessary for a technical process have not been achieved.

According to other prior art, propylene is converted to isobutyric acid in a two-step process. In the first method step, propylene and carbon monoxide are reacted in anhydrous hydrogen fluoride. The intermediate product is reacted in the second reaction step with an alcohol to form an ester. Although the first reaction step is concluded in 15 to 20 minutes, the second reaction step in general requires a longer reaction time. The total time for the method as a rule exceeds one hour. At at total reaction time of 30 minutes, only about one-half of the propylene introduced is converted into the isobutyric acid ester.

Considerably higher yields of carboxylic acids are obtained according to a one step method known in the art in which an approximately equimolar mixture of an olefin and water with carbon monoxide is reacted in a large excess of hydrogen fluoride serving as the catalyst. In order to obtain yields on the order of magnitude of 90 percent, reaction times of longer than 30 minutes, mostly longer than 60 minutes, are necessary at temperatures from 23° C. to 38° C.

Still other prior art teaches a method proceeding in the presence of a similarly large amount of hydrogen fluoride which contains from 5 to 30 percent of water or, if the preparation of the corresponding carboxylic acid ester is intended, of 2 to 15 mol percent of alcohol, at a temperature between −12° C. and 93° C. In this method, the temperature should be higher the higher the water content in the reaction mixture. Although the reaction time is reported as being in the general latitude of one minute to one hour, the practical performance of the method as a rule requires more than one hour.

Y. Takezaki et al. (Bull, Jap. Petrol. Inst. 8 3-38 (1966) have systematically investigated the Koch synthesis of isobutyric acid from propylene, water, and carbon monoxide in hydrogen fluoride and have determined an optimum for high yield and high reaction velocity. According to this optimum, 15 mols of hydrogen fluoride, which are mixed with 20 percent by weight of water, are employed per mol of propylene and the reaction is carried out at 94° C. under a total pressure of 190 atmospheres or more. Under these conditions, a yield of isobutyric acid which is 70 percent of theory is obtained in 20 minutes. At a higher or lower water content, the yield decreases, as it does also using a higher or lower reaction temperature. With increasing temperature, the formation of undesired oligomerization products of propylene increases. At pressures of 50 to 100 atmospheres, yields of only about 50 percent are obtained.

According to still other prior art, olefins having four or more carbon atoms are reacted with carbon monoxide and excess water at 20° C.–90° C. in the presence of hydrogen fluoride. Propylene is excluded as a starting material. In this method, high yields and selectivities for the corresponding carboxylic acids are obtained, particularly in a continuous mode of operation, if a saturated hydrocarbon is used as a diluent for the olefin. The necessary dwell time is 40 to 60 minutes.

From other prior art it is known to isomerize isopropylformiate under high pressure and at high temperature in N-methyl pyrrolidone with cobalt bromide as a catalyst. In contrast to the Koch synthesis, a mixture of iso-butyric and n-butyric acids is obtained according to this method, which mixture is difficult to separate distillatively. The total yield of both acids is 76 percent.

The long reaction times in the known discontinuous processes and the equally long dwell times in the aforementioned continuous process suggest that a continuous Koch synthesis of isobutyric acid from propylene, carbon monoxide, and water on a technical scale shows little promise, since in this case short dwell times and high yields and selectivities are indispensable. The finding reported by Takezaki et al. (loc. cit.) that the oligomerization of propylene increases considerably with increasing temperature counterindicates increasing the reaction velocity by an increase in the temperature above 94° C.

Indeed, the formation of oligomers proves to be the problem most difficult to overcome in the Koch synthesis with propylene. The fact that certain of the prior art discussed above is limited to the use of olefins with more than three carbon atoms, and that other art mentioned earlier may claim a reaction of propylene, but does not show such a reaction in a working example, is explained by this difficulty. Even higher olefins gives considerable, and often even predominant, amounts of oligomerization products, as is evident from the working examples found in the last-mentioned prior art patent. Even losses in yields of from 8 to 10 percent in the form of worthless oligomerization products, as are encountered in all known methods for carrying out the Koch synthesis with propylene, are unacceptable for the preparation of a basic material for the manufacture of synthetic resins.

The present invention has as its object the performance of this synthesis under conditions which permit a large-scale method for the preparation of isobutyric acid or its esters from propylene, carbon monoxide, and water or an alcohol. This includes a requirement for a continuous mode of operation, high yield and selectivity and therewith an extensive diminution of the oligomer problem, as well as a demand for a higher space-time yield, i.e. a short dwell time.

The recognition that high temperatures of at least 80° C. and particularly over 100° C.—which per se promote the formation of oligomers—were unavoidable in the interest of achieving a high reaction velocity preceded a solution to the problem. It was found that even under these conditions, oligomer formation can be significantly limited if the propylene concentration in the reaction mixture is continuously held below a low level. The realization of this principle led to the method described and claimed therein. A continuous mode of operation sets the condition for the introduction of propylene according to the size of the batch in process. A high backmixing of the reaction mixture is necessary in order to prevent any local increase in concentration at the point at which the propylene is introduced.

The propylene concentration is adjustable, at whatever reaction velocity prevails, by the speed of introducing the starting materials and, in this way, practically by the dwell time. The dwell time must in each case be sufficient for the almost complete reaction of the propylene which is introduced. By the term "propylene concentration" is to be understood the percentage content by weight of propylene in the total weight of the reaction mixture consisting of the liquid and gaseous phases.

It was not foreseeable that this problem of oligomer formation could be solved in a satisfactory manner by the claimed continuous method of operation at propylene concentrations below one percent, and preferably below 0.7 percent.

It has proved advantageous to maintain the content of water, or of a lower alcohol introduced for ester formation, in the reaction mixture at less than 5 mol percent, calculated on the hydrogen fluoride, and particularly below 2 mol percent. This is controllable by means of the amount of water or the amount of alcohol which is introduced. In this way, oligomer formation is suppressed further and the reaction velocity is increased at the same time, which in turn permits shorter dwell times. The mol ratio of propylene to water or alcohol should preferably be about equivalent, but can deviate from a 1:1 ratio to values between 1:0.8 and 1:2, in order to maintain the water or alcohol content in the reaction mixture at the desired level. The ratio of propylene to water or lower alcohol is advantageously 1:(0.9–1.1), particularly 1:(0.95–1.0). Hydrogen fluoride is preferably added in an amount from 5 to 15 mols, particularly from 7 to 12 mols, per mol of propylene or of isopropyl alcohol introduced.

Under optimum conditions, the method according to the invention permits the attainment of a total yield of isobutyric acid compounds of more than 90 percent of theory, of which more than 80% of theory is in the form of free isobutyric acid, at dwell times of only a few minutes and thereby opens for the first time the possibility of a technical scale synthesis of isobutyric acid.

When the direct formation of an ester of isobutyric acid is sought, then the corresponding alcohol is introduced instead of water. Above all, lower primary alkanols having one to four carbon atoms are employed. Methanol is the preferred alkanol. For the conversion of isobutyric acid compounds into methacrylic compounds, free isobutyric acid offers advantages over its esters. Hence, the preparation of the free acid, rather than the preparation of isobutyric acid esters, is the preferred embodiment of the invention.

The preferred starting materials for the method of the invention are propylene, carbon monoxide, and water or a lower alcohol. To the extent that binary addition compounds are formed from pairs of the materials present in the reaction mixture, these addition compounds can be used instead of or in addition to the components from which they are formed. Propylene can form isopropyl alcohol with one mol of water and can form diisopropyl ether with ½ mol of water. Isopropyl fluoride is easily formed with hydrogen fluoride. Carbon monoxide can be reacted with water to form formic acid, with a lower alcohol to form the corresponding formic acid ester, and with hydrogen fluoride to form formyl fluoride. A lower alcohol and propylene can give rise to the corresponding isopropyl alkyl ether. These binary addition products react according to the method of the present invention as easily as the components from which they are formed to produce isobutyric acid or its ester. Since they must be prepared in a special method step, their use, instead of or in addition to the components from which they are formed, is recommended only in exceptional cases. Among the aforementioned addition products, isopropyl alcohol takes a preferred position because of the ease with which it is formed. For example, it is obtained from a mixture of propylene and water on an acid ion exchanger. There are also ternary addition products of three component materials, namely isopropylformiate, which is comprised of propylene, carbon monoxide, and water. Isopropylformiate takes a special position as a starting material for the method of the present invention because its use in the method of the invention is not strictly governed by the narrow reaction conditions which pertain to mixtures of the components which form it or to the binary addition compounds.

The reaction of isopropylformiate to form isobutyric acid is a pure isomerization, so that no further starting materials are necessary. In any event, it is preferred to carry out the reaction in the presence of carbon monoxide, which is not used in the reaction and which can be completely recovered from the reaction mixture. The reaction temperature is in general between 20° C. and 150° C., preferably between 60° C. and 120° C. The dwell time in the reaction vessel can be between one minute and 200 minutes. Hydrogen fluoride is introduced in an amount of from 5 to 20 equivalents of acid per mol of isopropylformiate.

In the method of the present invention, the oligomerization reactions which occur extensively in other cases in which the Koch synthesis is used are largely absent, even in the method embodiment using isopropylformiate, so that a selectivity for isobutyric acid which nears 100 percent is attainable. Further, a practically quantitative reaction is attained.

Since the addition products in the reaction mixture in general decompose rapidly into their component parts, the limiting value specified herein for the propylene concentration, and, possibly, also for the water or alcohol concentration, must be observed in a corresponding fashion when determining the rate of addition or the dwell time.

The total pressure in the reactor is comprised of the partial pressures of propylene, carbon monoxide, hydrogen fluoride, and of the vapor pressure of the organic substances present in the liquid phase. The total pressure under the reaction conditions is preferably in the region from 50 to 150 atmospheres, particularly from 80 to 140 atmospheres. The CO partial pressure is at least 35 atmospheres, and preferably from 60 to 130 atmospheres.

In the preferred embodiment of the invention, which employs a mixture of propylene, carbon monoxide, and water or alcohol, or their aforementioned binary addition products, the materials are reacted continuously with a high degree of backmixing at a dwell time of the liquid phase of less than 20 minutes and at a temperature between 80° C. and 160° C., and the propylene content is maintained at less than one percent of the weight of the liquid phase.

The method can be carried out in a broad temperature range from 80° C. to 160° C., wherein the reaction velocity increases with temperature. The preferred temperature region extends from 100° C. to 140° C.

With dwell times of from 2 to 15 minutes, total yields over 90 percent of theory and selectivity for isobutyric acid above 93 percent are obtained at temperatures of 100° C.–120° C.

The method of the invention can be carried out in conventional pressure reactors with high backmixing, which reactors must be resistant to hydrogen fluoride under reaction conditions. As materials for the reaction, nickel or nickel alloys, such as "Monel", "Inconel", or "Hastelloy" are suitable. The size required for the pressure reactor is determined by the amount of material to be passed therethrough hourly and by the space-time yield. Since the cost of pressure reactors, particularly those made of special alloys, increases sharply with the size, the short dwell time permitted by the invention and the high space-time yields associated therewith advantageously affect plant costs. Contrasted with a dwell time of an hour, as is necessary for many known methods, the dwell times which can be attained according to the invention of, for example, 5 to 10 minutes, permit a decrease in reactor size to between a sixth and a twelfth of the size otherwise needed. The volumes of safety vessels and relief vessels are decreased in a similar measure.

In addition to simple stirred autoclaves, gas-liquid reactors having a dispersed gas phase come under consideration. Bubble columns or jet reactors, which facilitate an intimate contact of the liquid phase with the gas phase and a high circulation rate of the liquid reaction mixture, are of this type. The gaseous components of the reaction mixture, particularly propylene and carbon monoxide, are preferably mixed before entry into the reactor and are introduced as a gas mixture. Gas can be removed from the upper portion of the reactor and can again be mixed together with fresh gas for recycling.

The liquid phase of the reactor is continuously drawn off by way of a let-down valve and is worked up in the usual way. Preferably, the crude product is treated distillatively. In such a treatment, the low-boiling components, above all hydrogen fluoride and any unreacted propylene, are distilled off in a first distillation step at normal pressure or at a slight overpressure of, for example, four atmospheres, compressed, and reintroduced into the reactor. If a short distillation column is employed for this purpose, the hydrogen fluoride can be substantially completely separated from the organic reaction products.

All low-boiling by-products are volatilized together with the hydrogen fluoride, for example isopropyl alcohol, isopropyl fluoride, isobutyric acid fluoride, isobutyric acid isopropyl ester, and diisopropyl ether. They are returned to the reactor with the hydrogen fluoride and participate in further conversion to isobutyric acid. In part, they are readily decomposed with water. Thus, it is advantageous to add some water to the crude product during distillation and thus to promote the hydrolysis of isobutyric acid fluoride or of isobutyric acid isopropyl ester to isobutyric acid. The coproducts of the hydrolysis, namely hydrogen fluoride and isopropyl alcohol, are returned to the reactor.

The liquid portion of the crude product which remains after the first distillation step principally comprises isobutyric acid and small amounts of high-boiling oligomers of propylene and the like. In a second distillation step, preferably in a further short column, the isobutyric acid is evaporated and either condensed in known fashion or—preferably—led directly in vapor form to a reactor for oxidative dehydrogenation with formation of methacrylic acid. Since this reaction, or the plant installation used therefor, can be disturbed by hydrogen fluoride, the vaporized isobutyric acid is advantageously passed over a suitable absorption column. For a complete removal of hydrogen fluoride, a bauxite filling is suitable, for example. The high-boiling or non-volatile distillation residues are discarded or burned.

A better understanding of the present invention and of its many advantages will be had by referring to the following specific Example, given by way of illustration.

EXAMPLE 1

Continuous reaction of propylene, carbon monoxide, and water

The reaction is carried out in a stirred autoclave made of a nickel alloy ("Hastalloy C4") having a free reactor volume of 60 ml and equipped with a gas-treatment stirrer. The stirring velocity is about 1,000 rpm. The autoclave is equipped with a gas inlet passing through the stirrer as well as further inlets and outlets and can be warmed with an electric heater.

Carbon monoxide is introduced in part through the gas-treatment stirrer. The remaining components are pumped in through separate conduits.

Propylene, water, technical grade hydrogen fluoride, and carbon monoxide are reacted at reactor temperatures of 100° C. and 120° C. and an operating pressure of 120 atmospheres at a mol ratio of 1:0.98:10:1.5. The dwell time is varied between 4 and 15 minutes by alteration of the throughput amount. In a stationary state, the following yields and selectivities are attained.

| Dwell time (min.) | Reaction temperature = 100° C. | | | | Reaction temperature = 120° C. | | | |
|---|---|---|---|---|---|---|---|---|
| | Propylene conc. (W. %)** | Yield IBS* (%) | Oligomers (%) | Selectivity of IBS (%) | Propylene conc. (W. %)** | Yield IBS* (%) | Oligom. (%) | Selectivity of IBS (%) |
| 4 | 0.31 | 81 | 5.5 | 86 | 0.12 | 91 | 3.5 | 95 |
| 7.5 | 0.12 | 82 | 3.8 | 92 | 0.07 | 93 | 1.5 | 96 |
| 15 | 0.09 | 94 | 1.9 | 96 | 0.04 | 94 | 2.0 | 96 |

*IBS = isobutyric acid and derivatives which can be hydrolyzed to form isobutyric acid, particularly the isopropyl ester.
**propylene concentration in the reaction mixture in percent by weight of the total reaction mixture.

At a dwell time of 3 minutes, the propylene:water ratio was varied between 1:0.96 and 1:0.99. The following results were obtained at 120° C.

| Propylene/water (mol) | Yield of IBS (%) | Selectivity (%) |
| --- | --- | --- |
| 1:0.96 | 85 | 91 |
| 1:0.97 | 89 | 93 |
| 1:0.98 | 92 | 95 |
| 1:0.99 | 89 | 93 |

EXAMPLE 2

Continuous reaction of isopropylformiate and carbon monoxide

A reaction mixture of isopropylformiate, technical grade hydrogen fluoride, and carbon monoxide in a mol ratio of 1:10:0.5 were reacted continuously in the apparatus described in Example 1 at 70° C. and at 120° C.

Results:

| | | |
| --- | --- | --- |
| Reaction temperature | 70° C. | 120° C. |
| Dwell time | 30 min. | 5 min. |
| Pressure in the reactor | 100 atmospheres | 110 atmospheres |
| Yield of isobutyric acid | 97% | 98% |
| Selectivity | greater than 98% | greater than 98% |

EXAMPLE 3

Following the procedure of Example 1 propanol-2, hydrogen fluoride, and carbon monoxide in a mole ratio of 1:10:1.5 are reacted at 120° C. and an operating pressure of 120 atmospheres, the dwell time being 15 minutes. Under stady state conditions IBS (as explained in Example 1) is obtained in a yield of 94%. The selectivity is 97%, calculated on the propanol-2 feed. Oligomers are formed in a yield of less than 2 percent of the propanol-2 feed.

EXAMPLE 4

Following the procedure of Example 1 propylene, ethanol, hydrogen fluoride, and carbon monoxide in a mole ratio of 1:1.2:10:1.5 are reacted at 110° C. and an operating pressure of 130 atmospheres within a dwell time of 15 minutes. Under stady state conditions isobutyric acid ethyl ester is produced in a 89 percent yield and a selectivity of 92 percent, calculated on added propylene. Oligomers are formed in a yield of about 2.5 percent of the propylene feed.

What is claimed is:

1. A continuous one-step method for the preparation of isobutyric acid which comprises continuously rearranging isopropyl formiate in the presence of a catalyst consisting essentially of 5 to 20 equivalents of hydrogen fluoride per mol of isopropyl formiate at a temperature between 20° C. and 150° C. at a dwell time of said isopropyl formiate between one and 200 minutes.

2. A method as in claim 1 wherein carbon monoxide is present.

* * * * *